United States Patent
Bousquet et al.

(10) Patent No.: US 8,917,090 B2
(45) Date of Patent: Dec. 23, 2014

(54) NONDESTRUCTIVE TEST OF A SEALING MEMBER

(75) Inventors: Sadia Bousquet, Moissy Cramayel (FR); Gerard Derrien, Houilles (FR); Carolina Garcia-Lopez, Guyancourt (FR); Jean-Jacques Nedelec, Le Mesnil Saint Denis (FR)

(73) Assignee: SNECMA, Paris (FR)

( * ) Notice: Subject to any disclaimer, the term of this patent is extended or adjusted under 35 U.S.C. 154(b) by 384 days.

(21) Appl. No.: 13/377,286

(22) PCT Filed: Jun. 2, 2010

(86) PCT No.: PCT/FR2010/051077
§ 371 (c)(1),
(2), (4) Date: Mar. 2, 2012

(87) PCT Pub. No.: WO2010/142887
PCT Pub. Date: Dec. 16, 2010

(65) Prior Publication Data
US 2012/0153941 A1 Jun. 21, 2012

(30) Foreign Application Priority Data
Jun. 10, 2009 (FR) .................................... 09 53839

(51) Int. Cl.
*G01N 27/90* (2006.01)
*F04D 29/10* (2006.01)
*F01D 11/00* (2006.01)
*F04D 27/00* (2006.01)

(52) U.S. Cl.
CPC .............. *F04D 29/102* (2013.01); *F01D 11/00* (2013.01); *F04D 27/001* (2013.01); *G01N 27/902* (2013.01); *G01N 27/9053* (2013.01); *F05D 2260/80* (2013.01)
USPC .............................................. 324/238; 73/618

(58) Field of Classification Search
CPC .. G01N 27/9013; G01N 29/22; G01N 27/902
USPC ..................................... 324/238, 240; 73/618
See application file for complete search history.

(56) References Cited

U.S. PATENT DOCUMENTS

| 6,792,809 B1 * | 9/2004 | Moore .............................. 73/618 |
| 2002/0079889 A1 * | 6/2002 | Givens et al. .................. 324/240 |

(Continued)

FOREIGN PATENT DOCUMENTS

| EP | 1 605 259 | 12/2005 |
| EP | 1 780 538 | 5/2007 |

(Continued)

OTHER PUBLICATIONS

International Search Report Issued Oct. 13, 2010 in PCT/FR10/51077 Filed Jun. 2, 2010.

(Continued)

*Primary Examiner* — Arleen M Vazquez
*Assistant Examiner* — Brent J Andrews
(74) *Attorney, Agent, or Firm* — Oblon, Spivak, McClelland, Maier & Neustadt, L.L.P.

(57) ABSTRACT

A device for inspecting an annular sealing wiper extending at the surface of a bladed-wheel drum of a rotor. The device includes a carriage including at least two guide wheels and carrying a probe situated in a location such that, when the carriage is in position, the probe is positioned facing an edge of the wiper for inspection and at a determined distance therefrom.

13 Claims, 4 Drawing Sheets

(56) References Cited

U.S. PATENT DOCUMENTS

| | | |
|---|---|---|
| 2005/0274188 A1* | 12/2005 | Cabanis et al. ............... 73/618 |
| 2006/0213274 A1 | 9/2006 | Moore et al. |
| 2007/0096728 A1* | 5/2007 | Mader Viertl ............... 324/240 |
| 2009/0126493 A1* | 5/2009 | Moore et al. ............... 73/618 |

FOREIGN PATENT DOCUMENTS

| | | |
|---|---|---|
| JP | 2005-195472 A | 7/2005 |
| JP | 2005-208061 A | 8/2005 |
| JP | 2009-104121 A | 5/2009 |
| RU | 2 033 566 C1 | 4/1995 |
| WO | 2006 101586 | 9/2006 |

OTHER PUBLICATIONS

Office Action issued Feb. 26, 2014 in Russian Application No. 2011154350 (With English Translation).

Japanese Office Action issued Jun. 3, 2014 in Patent Application No. 2012-514516 with English Translation.

* cited by examiner

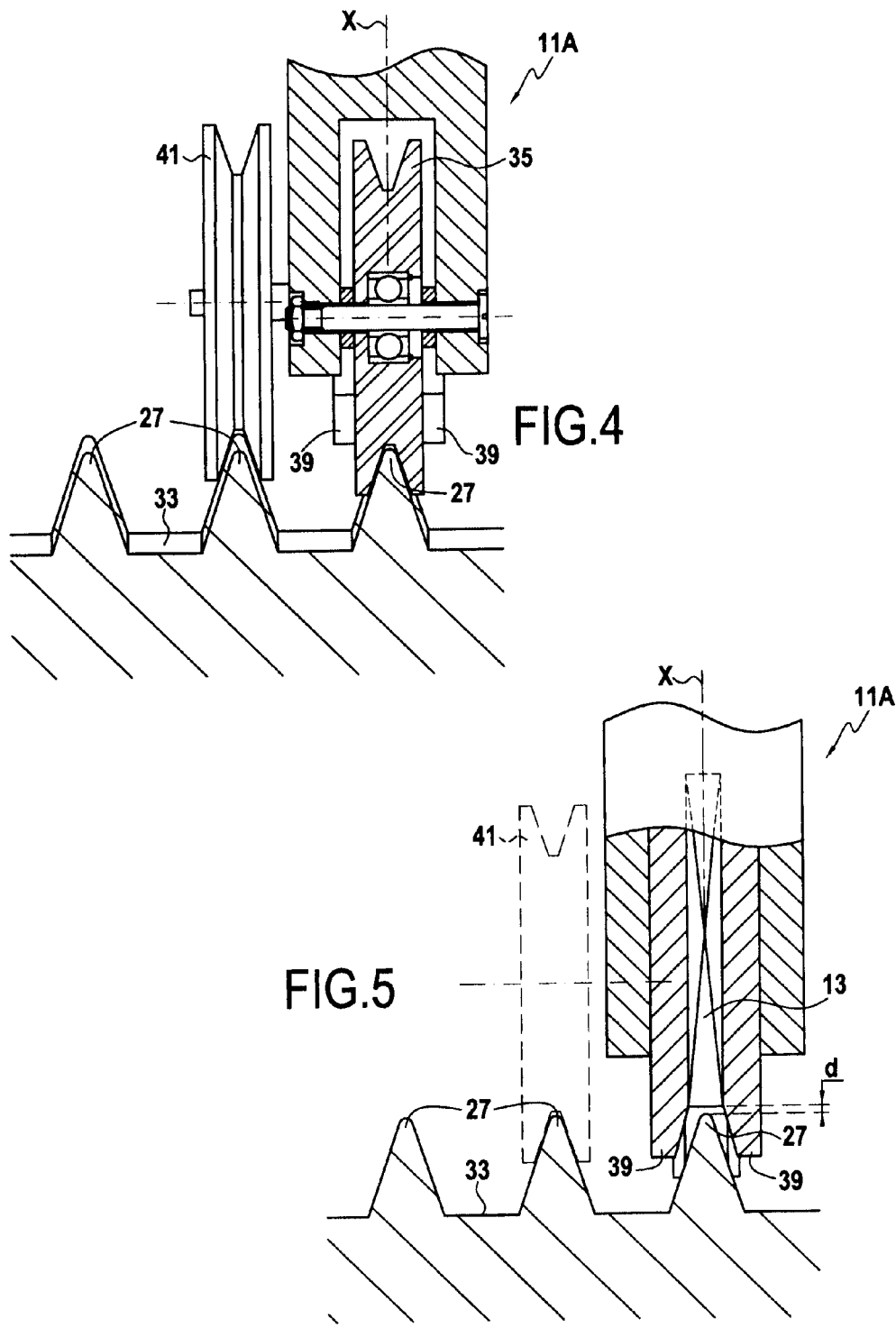

NONDESTRUCTIVE TEST OF A SEALING MEMBER

BACKGROUND OF THE INVENTION

1. Field of the Invention

The invention relates to non-destructive inspection of an annular sealing wiper extending at the surface of a bladed wheel drum of a turbine engine. More particularly, it relates to eddy current inspection of the edges of wipers that extend generally in groups of several wipers, each group being situated between the disks making up such a drum.

2. Description of the Related Art

In an airplane turbojet, a turbomachine such as a compressor has a bladed wheel drum mounted to rotate about its main axis. This drum, often referred to as a "spool", carries all of the rotor blades. Each stage of the compressor has a ring of movable blades that are regularly spaced apart at the periphery of a disk. The assembled-together disks constitute the above-mentioned drum.

Between the rings of movable blades there are arranged rings of stator vanes. Sealing between two successive stages is obtained by co-operation between a ring of abradable material that is carried by the stationary vanes, and wipers that are secured to said drum. The wipers constitute kinds of rough annular ribs. Between two successive stages, sealing is generally provided by a plurality of parallel wipers (generally two to four of them).

In order to limit wiper wear over time, a strong material is deposited thereon, by means of a plasma method. This plasma deposit needs to be subjected to non-destructive inspection in order to identify any type of crack fault. The non-destructive inspection means most commonly used involve eddy current inspection. This type of inspection has until now been performed using a probe (high frequency coil) having an end that is moved along the edge of the wiper for inspection, while remaining directly in contact therewith.

Plasma deposition involves a certain amount of roughness on the wiper and this leads to the probe being worn rapidly. Attempts have been made to remedy that problem by covering the wiper and the end of the probe in a film of polytetrafluoroethylene in order to protect the probe, to ensure good effectiveness of eddy current inspection, and to achieve low friction while the probe is moving relative to the wiper. That solution requires a very lengthy preparation time, in particular for depositing the film on each wiper. Those operations occupy several hours and there is also the cost of the film of polytetrafluoroethylene.

BRIEF SUMMARY OF THE INVENTION

The invention enables all of those problems to be solved by preferring contactless non-destructive inspection using a probe, and thus not subjecting it to wear, and without making any use of polytetrafluoroethylene.

More particularly, the invention provides a device for inspecting an annular sealing wiper forming part of a sealing structure extending at the surface of a bladed-wheel drum, the device being characterized in that it comprises a carriage having at least two spaced-apart guide wheels suitable for coming into contact with at least a portion of said sealing structure that forms a circular rail, and in that said carriage carries at least one probe situated at a location such that, when said wheels are in engagement with said circular rail, the probe is to be found positioned facing an edge of said wiper for inspection and at a determined distance therefrom.

The fact of using the wipers as a reference for the running of the carriage makes it possible to guarantee that the distance between the probe and the part for inspection is indeed constant, a condition that is necessary for good inspection, particularly if the inspection is performed by eddy currents.

In the above description, the above-mentioned sealing structure relates to at least one wiper, and most often to a group of wipers that are close together and axially offset on the surface of said drum, between two adjacent disks. It is the sealing structure as a whole that forms said circular rail. In other words, one of the above-mentioned wheels may have a V-section groove whereby it becomes engaged on the top of a wiper, or else it may have a convex profile that is engaged between two adjacent wipers.

BRIEF DESCRIPTION OF THE SEVERAL VIEWS OF THE DRAWINGS

The invention can be better understood and other advantages thereof appear more clearly in the light of the following description of an inspection device in accordance with the principle of the invention, given purely by way of example and made with reference to the accompanying drawings, in which:

FIG. 4 is a section on IV-IV of FIG. 3;

FIG. 5 is a section on V-V of FIG. 3; and

DETAILED DESCRIPTION OF THE INVENTION

Figure 1:
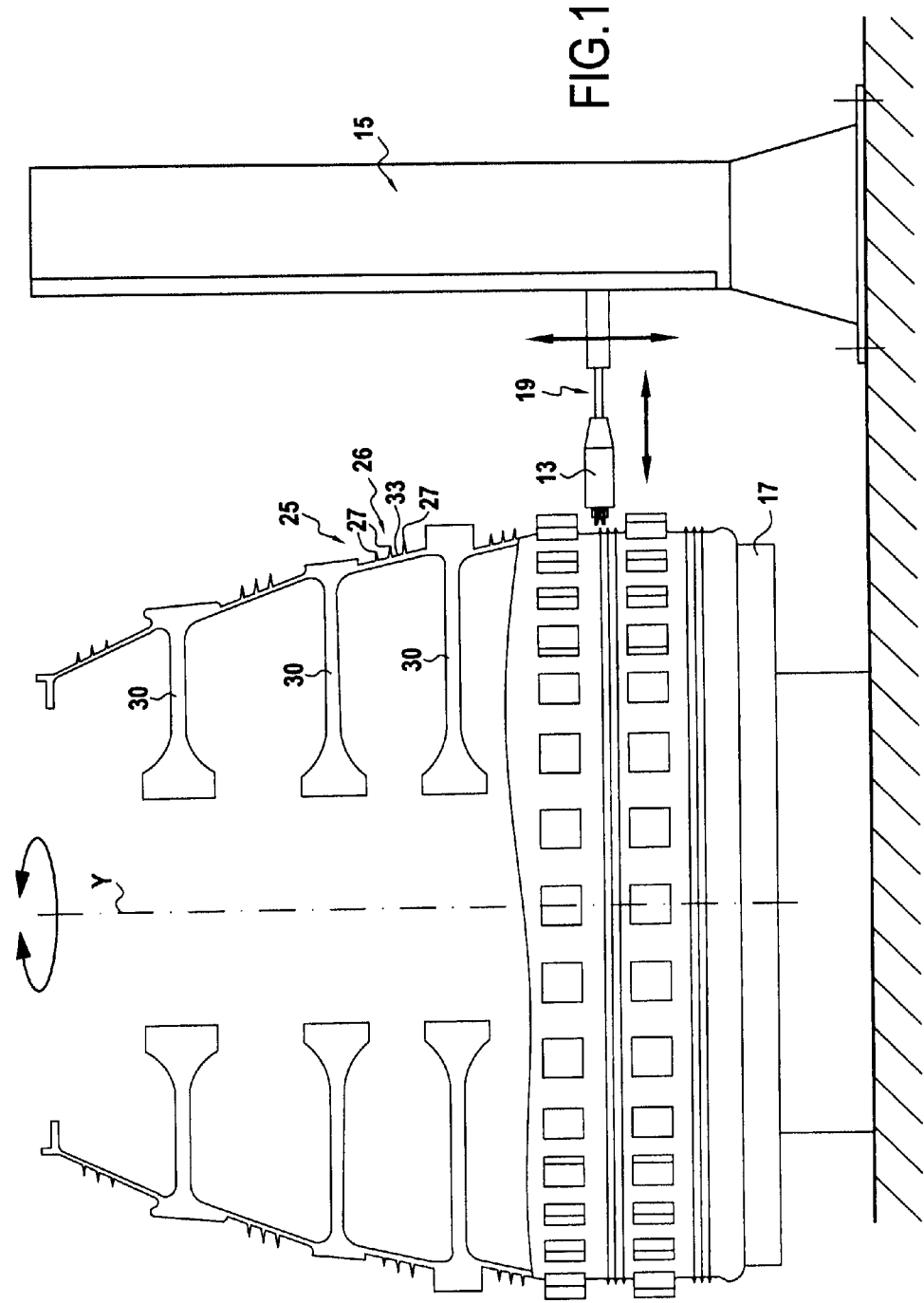
FIG. 1 is a diagrammatic overall view of an inspection device of the invention, with programmed automatic positioning of the probe.
Figure 2:
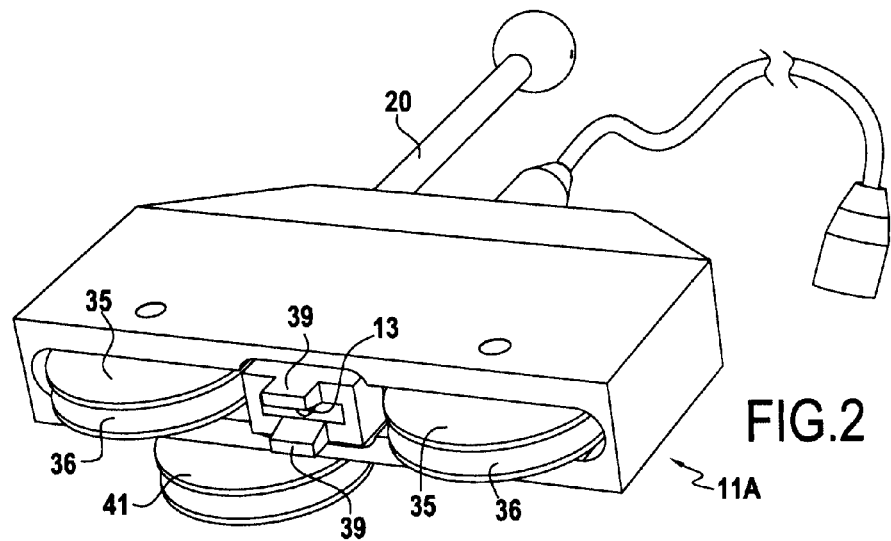
FIG. 2 is a diagrammatic view of a carriage carrying such a probe for manual exploration.
Figure 3:
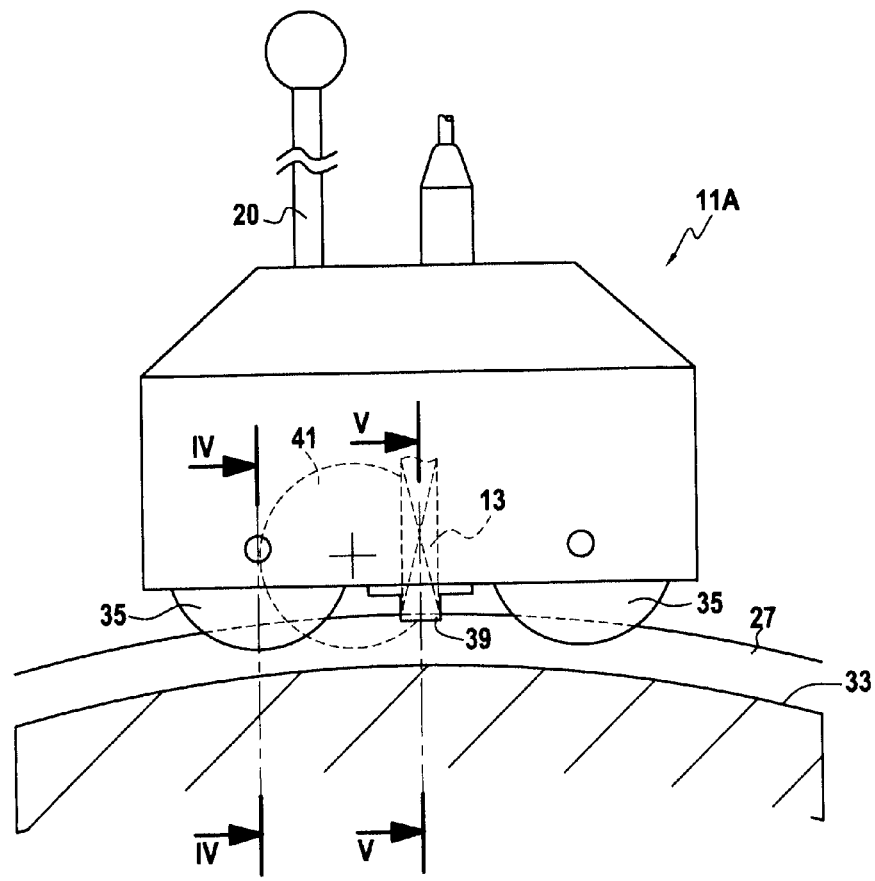
FIG. 3 is a diagram illustrating inspection of a wiper using the carriage of FIG. 2.

The inspection device shown in FIG. 1, in an automatic version, comprises a carriage 11 carrying at least one eddy current probe 13, a robot 15 carrying the carriage, and a turntable 17 mounted to rotate about an axis of rotation Y, which axis is vertical in this example. The robot 15 has a telescopic arm 19, and the carriage 11 is mounted at the end of the arm. The arm 19 is horizontal and is itself movable vertically. The robot is programmed to adjust the position of the carriage relative to the turntable so as to inspect the various wipers of a drum 25 placed on the turntable.

In the example shown, such a drum 25 is placed on the turntable and is positioned in such a manner that its main axis of symmetry coincides with the vertical axis of rotation Y of the turntable 17. As shown, the bladed wheel drum 25 as placed on the turntable is made up of adjacent disks 30 that are welded to one another. Between two consecutive disks, the drum carries a sealing structure 26 made up of a plurality of wipers 27. Each wiper is in the form of a rough rib. The robot 15, located close to the turntable, is of a kind that enables the carriage to be brought to face each group of wipers 27 (referred to above as a sealing structure). The same height setting for the carriage makes it possible to inspect all of the wipers 27 in a given sealing structure 26, either in succession, or else simultaneously if the carriage has a plurality of probes.

The wipers 27 in a given sealing structure are arranged side by side and they are spaced apart by a small axial distance, so that they define grooves 33 between one another. Thus, the wipers, like the grooves, can act as references for guiding the carriage 11.

The carriage 11A shown in FIGS. 2 to 5 is more particularly adapted for manual inspection. That is why the rod 19 is replaced with a handle 20. Nevertheless, the carriage 11A is essentially similar to the carriage 11.

More precisely, the carriage 11A has at least two spaced-apart guide wheels 35 suitable for coming into contact with at least a portion of said sealing structure 26 that acts generally as a circular rail. In this example, the two guide wheels 35 are situated in the same plane. In the example, the wheels are of the type having a groove 36 and they are designed to come into contact with the circular edge of a wiper. The probe 13 is constituted by a coil presenting an axis X (the axis of its turns) that is designed to be held substantially perpendicularly relative to the part for inspection. The probe 13, and more particularly one end thereof, is situated at a location such that it is positioned facing an edge of the wiper 27 for inspection when the wheels 35 are in engagement with said circular rail. In this example, the wiper for inspection is the wiper on which the wheels 35 are engaged. The axis X of the probe and the bottoms of the grooves in the wheels 35 are thus substantially in the same plane. The probe 13 is situated between the two wheels. FIG. 4 shows a wheel 35 engaged on the wiper 27 that guides it. FIG. 5 shows the position of the probe 13 (the coil) relative to the edge of the wiper 27 for inspection. When the wheels 35 are engaged with the wiper 27, it can be seen that the end of the probe that is closest to the wiper is not in contact therewith, but is held at a small predetermined distance $\underline{d}$ from the edge of said wiper for inspection. Throughout the movement of the carriage 11A along the wiper, this distance remains constant, where this feature constitutes one of the conditions necessary for good inspection. Furthermore, it should be observed that the carriage includes lateral flanks 39 extending on either side of the end of the probe and suitable for facing the wiper for inspection. These lateral flanks are useful when performing control manually, i.e. when not using the robot. It suffices for the operator to engage the wheels on the wiper for inspection and to move the carriage all around the drum. Under such circumstances, the lateral flanks 39 enable the operator to verify the orientation of the probe relative to the wiper.

In addition, the carriage 11A includes at least one additional guide wheel 41 that is situated in a plane parallel to the plane that contains the other two. This additional guide wheel is suitable for coming into contact with the circular rail, e.g. with an adjacent wiper 27 (or with a groove 33 defined between two wipers). This additional guide wheel also contributes to stabilizing the orientation of the probe relative to the wiper for inspection.

In the automatic embodiment of FIG. 1, the lateral flanks 39 and the additional wheel 41 are not necessary.

Figure 6:
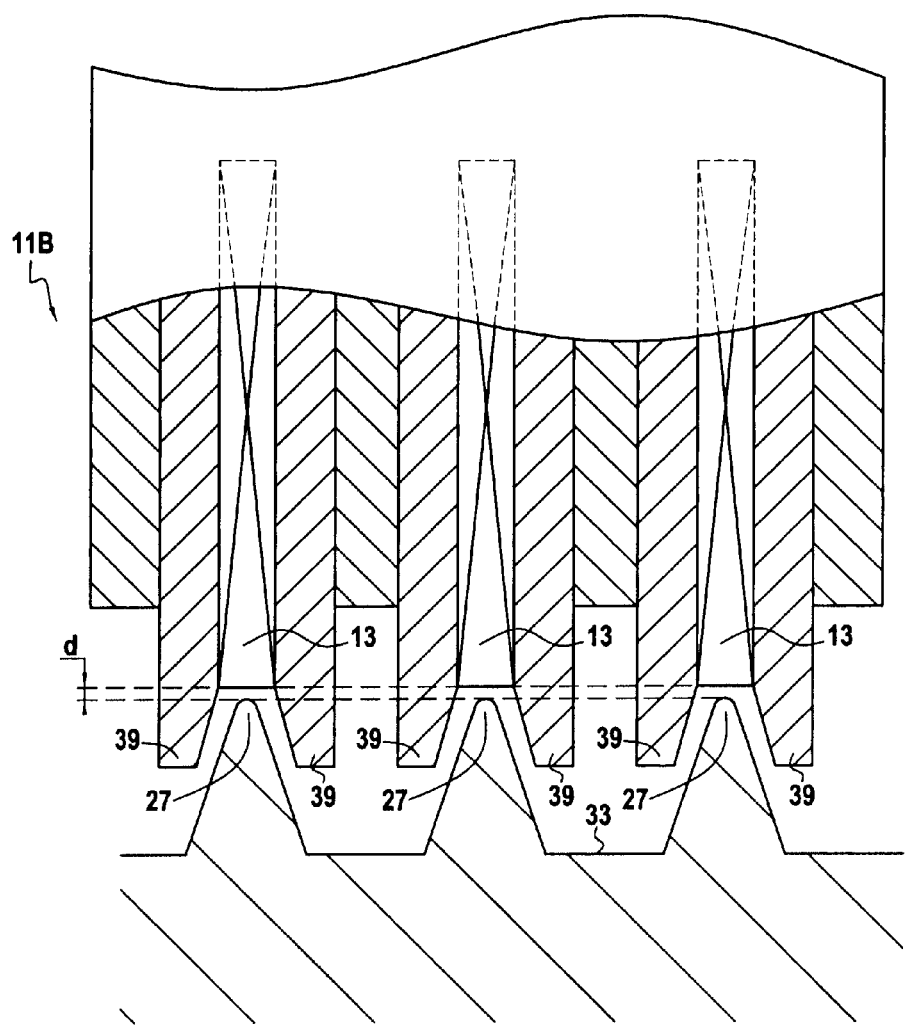
FIG. 6 is a section view, similar to that of FIG. 5, showing a variant of the carriage enabling all of the wipers of a given sealing structure to be inspected simultaneously.

In the variant of FIG. 6, the carriage 11B carries a plurality of probes 13 that are spaced apart such that each of them is positioned facing an edge of a corresponding wiper 27 in a single sealing structure and at a determined distance $\underline{d}$ therefrom. This enables all of the wipers in a given group to be inspected simultaneously.

By way of example, in the automatic version of FIG. 1, the robot is programmed to bring the carriage 11B to an altitude corresponding to the position of a group of wipers, and if the carriage has a number of probes 13 that corresponds to the number of wipers 27 in this group, with said probes being spaced apart by the same distance as the distance by which the wipers are spaced apart from one another, then all of the wipers in a given group (or given sealing structure) can be inspected at the same time, in one revolution of the turntable 17.

Depending on the stage in which they are to be found, the wipers may be spaced apart by differing distances. It is possible to have carriages with probes at different spacings. In a variant, the carriage may include means for adjusting the spacing between said probes.

The invention claimed is:

1. A device for inspecting an annular sealing wiper forming part of a sealing structure extending at an external surface between two disks of a bladed-wheel drum, comprising:
   a carriage including at least two spaced-apart guide wheels configured to come into contact with at least a portion of the sealing structure on the external surface that forms a circular rail; and
   wherein the carriage carries at least one probe situated at a location such that, when the wheels are in engagement with the circular rail, the probe is to be found positioned facing an edge of the wiper for inspection and at a determined distance therefrom.

2. The device according to claim 1, wherein the wheels are of grooved type, and wherein an axis of the probe and bottoms of the grooves of the wheels are substantially coplanar, the probe being situated between the two wheels.

3. The device according to claim 1, wherein the carriage includes lateral flanks extending on either side of an end of the probe that is configured to face the wiper for inspection.

4. The device according to claim 2, wherein the carriage includes at least one additional guide wheel situated in a plane parallel to the plane containing the other two guide wheels and configured to come into contact with the circular rail so as to stabilize orientation of the probe relative to the wiper for inspection.

5. The device according to claim 3, wherein the carriage includes at least one additional guide wheel situated in a plane parallel to the plane containing the other two guide wheels and configured to come into contact with the circular rail so as to stabilize orientation of the probe relative to the wiper for inspection.

6. The device according to claim 1, wherein the carriage includes a plurality of probes that are spaced apart such that each of them is positioned facing and at a predetermined distance from a corresponding wiper edge during inspection.

7. The device according to claim 6, wherein the carriage includes means for adjusting the spacing between the probes.

8. The device according to claim 1, further comprising a turntable for rotating about an axis of rotation and configured to receive the drum, the drum being positioned such that its main axis of symmetry coincides with the axis of rotation of the turntable.

9. The device according to claim 8, further comprising a robot including an arm, and wherein the carriage is mounted at an end of the arm, the robot being programmed to adjust the position of the carriage relative to the turntable to inspect various wipers of the drum.

10. The device according to claim 1, wherein the or each probe is an eddy current probe.

11. The device according to claim 1, wherein the probe is free of contact with the edge of the wiper when the wheels are in engagement with the circular rail.

12. The device according to claim 2, wherein the grooves of the wheels are tapered so as to present a shape similar to a shape of the wiper.

13. A method for inspecting an annular sealing wiper forming part of a sealing structure extending at an external surface between two disks of a bladed-wheel drum, comprising:

providing a carriage including at least one probe and at least two spaced-apart guide wheels configured to come into contact with at least a portion of the sealing structure on the external surface that forms a circular rail;

positioning the carriage so that the wheels are in engagement with the circular rail and the probe is positioned facing an edge of the wiper at a determined distance therefrom; and inspecting the wiper using the probe.

* * * * *